United States Patent
Yang

(10) Patent No.: US 8,147,880 B2
(45) Date of Patent: *Apr. 3, 2012

(54) POLYACETYLENIC COMPOUNDS FOR STIMULATING INSULIN GENE EXRESSION, PRODUCTION AND SECRETION

(75) Inventor: Wen-Chin Yang, Taichung County (TW)

(73) Assignee: Academia Sinica, Taipei (TW)

( * ) Notice: Subject to any disclaimer, the term of this patent is extended or adjusted under 35 U.S.C. 154(b) by 14 days.

This patent is subject to a terminal disclaimer.

(21) Appl. No.: 12/766,895

(22) Filed: Apr. 25, 2010

(65) Prior Publication Data

US 2010/0204166 A1 Aug. 12, 2010

Related U.S. Application Data

(63) Continuation of application No. 11/674,105, filed on Feb. 12, 2007, now Pat. No. 7,763,285.

(51) Int. Cl.
*A61K 36/00* (2006.01)

(52) U.S. Cl. ........................................ 424/725; 514/866

(58) Field of Classification Search .................. None
See application file for complete search history.

(56) References Cited

FOREIGN PATENT DOCUMENTS

| JP | 2004083463 A | * | 3/2004 |
| JP | 2004352680 A | * | 12/2004 |
| JP | 2005298372 A | * | 10/2005 |

OTHER PUBLICATIONS

Chang et al, The distinct effects of a butanol fraction of Bidens pilosa plant extract on the development of Th1-mediated diabetes and Th2-mediated airway inflammation in mice, Journal of biomedical science, (2005) vol. 12, No. 1, pp. 79-89.*

European Patent Office Communication dated May 9, 2011, indicating grant and the allowed claims for the European counterpart application (No. 08101484.7) of the instant application. Allowed claims are shown on pp. 16-17.

* cited by examiner

*Primary Examiner* — Qiuwen Mi
(74) *Attorney, Agent, or Firm* — Hsiu-Ming Saunders; Intellectual Property Connections, Inc.

(57) ABSTRACT

This invention relates to a method of treating type II diabetes with a polyacetylenic compound of the following formula:

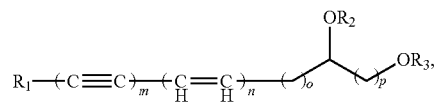

in which $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is H or a monosaccharide residue; $R_3$ is H or $C_1$-$C_{10}$ alkyl; m is 2, 3, or 4; n is 0, 1, 2, or 3; o is 0, 1, 2, 3, or 4; and p is 1, 2, 3, or 4.

1 Claim, No Drawings

POLYACETYLENIC COMPOUNDS FOR STIMULATING INSULIN GENE EXRESSION, PRODUCTION AND SECRETION

REFERENCE TO RELATED APPLICATION

This application is a continuation application, and claims benefit of U.S. patent application Ser. No. 11/674,105, filed Feb. 12, 2007, which status is granted and issued as U.S. Pat. No. 7,763,285, the disclosure of which is hereby incorporated by reference in its entirety.

BACKGROUND OF THE INVENTION

Type II diabetes is a disease marked by hyperglycemia, i.e., high levels of glucose in the blood. Many patients of type II diabetes suffer various life-threatening complications resulting from long-term hyperglycemia. Effective control of blood glucose levels is the key to preventing or reversing diabetic complications.

Insulin secretion plays an important role in regulating blood glucose levels. Therefore, there is a need to identify compounds that enhance insulin secretion, thereby effectively treating type II diabetes.

SUMMARY OF THE INVENTION

This invention is based on the unexpected finding that a naturally occurring polyacetylenic compound was effective in treating type II diabetes.

In one aspect, this invention features a pure compound of formula (I):

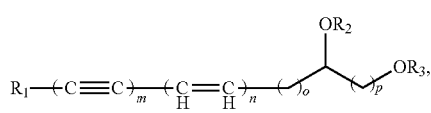

In this formula, $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is a monosaccharide residue; $R_3$ is H or $C_1$-$C_{10}$ alkyl; m is 2, 3, or 4; n is 0, 1, 2, or 3; o is 0, 1, 2, 3, or 4; and p is 1, 2, 3, or 4. The term "pure compound" refers to a compound that has a purity of at least 80% (e.g., 95% or 99%). Referring to formula (I), a subset of the polyacetylenic compounds described above are those in which $R_1$ is $C_1$-$C_{10}$ alkyl (e.g., methyl), $R_2$ is glycopyranose; $R_3$ is H or $C_1$-$C_{10}$ alkyl; m is 4; n is 0; o is 2; and p is 1.

The term "alkyl" refers to a saturated, linear or branched, non-aromatic hydrocarbon moiety, such as $CH_3$, —$CH_2$—, or branched $(CH_3)_2CH_2$—. The term "alkenyl" refers to a linear or branched, non-aromatic hydrocarbon moiety having at least one double bond, such as $CH_2$=CH—, or —CH=CH—. The term "alkynyl" refers to a linear or branched, non-aromatic hydrocarbon moiety having a least one triple bond, such as CH≡C— or —C≡C—. The term "cycloalkyl" refers to a saturated non-aromatic cyclic hydrocarbon moiety, such as cyclohexyl. The term "cycloalkenyl" refers to a non-aromatic, cyclic hydrocarbon moiety that contains at least one double bond in the ring, such as cyclohexenyl. The term "heterocycloalkyl" refers to a saturated non-aromatic, cyclic moiety having at least one ring heteroatom (e.g., O, N, or S), such as 4-tetrahydropyranyl. The term "heterocycloalkenyl" refers to a non-aromatic, cyclic moiety having at least one ring heteroatom and at least one double bond in the ring, such as pyranyl. The term "aryl" refers to a hydrocarbon moiety having at least one aromatic ring. Examples of aryl moieties include phenyl, phenylene, biphenyl, naphthyl, naphthylene, pyrenyl, anthryl, and phenanthryl. The term "heteroaryl" refers to a moiety having at least one aromatic ring which contains at least one heteroatom. Examples of heteroaryl moieties include furyl, furylene, fluorenyl, pyrrolyl, thienyl, oxazolyl, imidazolyl, thiazolyl, pyridyl, pyrimidinyl, quinazolinyl, isoquinolyl, and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties. Examples of substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfony, arylsulfonyl, heteroarylsulfonyl, $C_1$-$C_{10}$ alkylsulfonamide, arylsulfonamide, heteroarylsulfonamide $C_1$-$C_{10}$ alkylimino, arylimino, $C_1$-$C_{10}$ alkylsulfonimino, alrylsulfonimino, hydroxyl, halo, thio, $C_1$-$C_{10}$ alkylthio, arylthio, aminothioacyl, amidino, guanidine, ureido, cyano, nitro, nitroso, azido, acyl, thioacyl, acyloxy, carboxyl, amido, carbamoyl, and carboxyl, and carboxylic ester. Examples of substituents on alkyl, alkenyl, and alkynyl include all of the above-recited substituents except $C_1$-$C_{10}$ alkyl, $C_2$-$C_{10}$ alkenyl, and $C_2$-$C_{10}$ alkynyl. Cycloalkyl, cycloalkenyl, heterocycloalkyl, heterocycloalkenyl, aryl, and heteroaryl can also be fused with each other.

In another aspect, this invention features a method for treating type II diabetes by administering to a subject in need an effective amount of a polyacetylenic compound of formula (I) shown above, in which $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{10}$ cycloalkenyl, heterocycloalkyl, $C_1$-$C_{20}$ heterocycloalkenyl, aryl, or heteroaryl; $R_1$ is H or a monosaccharide residue; $R_3$ is H or $C_1$-$C_{10}$ alkyl; m is 2, 3, or 4; n is 0, 1, 2, or 3; o is 0, 1, 2, 3, or 4; and p is 1, 2, 3, or 4. A subset of the polyacetylenic compounds are those in which $R_1$ is $C_1$-$C_{10}$ alkyl (e.g., methyl); $R_2$ is a glucose, galactose, fucose, mannose, gulose residue, or H; $R_3$ is H; m is 4, n is 0, o is 2, and p is 1. A polyacetylenic compound can be administered to the subject as a pure compound in a pharmaceutical composition or as a component in a *Bidens pilosa* extract (see below).

In a further aspect, this invention features a method for treating type II diabetes by administering to a subject in need an effective amount of a *Bidens pilosa* preparation. Such a preparation can be obtained by stirring pulverized *Bidens pilosa* plants in water at an elevated temperature (e.g., at 50° C. or 100° C.) to form a suspension, and collecting a supernatant of the suspension. The supernatant can be further extracted with an alcohol (e.g., n-butanol) to provide an enriched preparation. The *Bidens pilosa* preparation contains one or more of the polyacetylenic compounds of the just-mentioned formula (I). For example, it contains cytopiloyne:

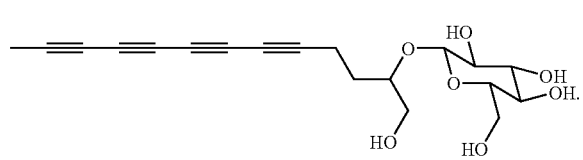

The polyacetylenic compounds described above include the compounds themselves, as well as their salts, prodrugs, and solvates, if applicable. Such salts, for example, can be formed by interaction between a negatively charged substituent (e.g., carboxylate) on a polyacetylenic compound and a cation. Suitable cations include, but are not limited to, sodium ion, potassium ion, magnesium ion, calcium ion, and an ammonium cation (e.g., tetramethylammonium ion). Likewise, a positively charged substituent (e.g., amino) on a polyacetylenic compound can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing above compounds described above. A solvate refers to a complex formed between a polyacetylenic compound and a pharmaceutically acceptable solvent. Examples of pharmaceutically acceptable solvents include water, ethanol, isopropanol, n-butanol, ethyl acetate, and acetic acid.

The polyacetylenic compounds may contain one or more asymmetric centers or a non-aromatic double bond. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a composition, including a *Bidens pilosa* extract, containing one or more of the polyacetylenic compounds described above for use in treating type II diabetes, and the use of such a composition for the manufacture of a medicament for the just-mentioned treatment.

The details of the embodiments of the invention are set forth in the description below. Other features, objects, and advantages of the invention will be apparent from the following description and from the claims.

DETAILED DESCRIPTION OF THE INVENTION

This invention relates to using polyacetylenic compounds for treating type II diabetes.

Some of the polyacetylenic compounds (e.g., cytopiloyne) can be isolated from *Bidens pilosa* as follows. Whole *Bidens pilosa* plants are first pulverized and then stirred in heated water. After removal of insoluble materials (e.g., by filtration, decantation, or centrifugation), the resultant supernatant is subjected to liquid chromatography (e.g., high-pressure liquid chromatography) or other suitable methods to afford pure polyacetylenic compounds. The pure compounds thus obtained can be further derivatized to provide a number of other polyacetylenic compounds of this invention.

The polyacetylenic compounds described above can also be prepared by conventional methods. Below are three reaction schemes illustrating synthetic routes to a polyacetylenic compound of this invention.

Scheme 1

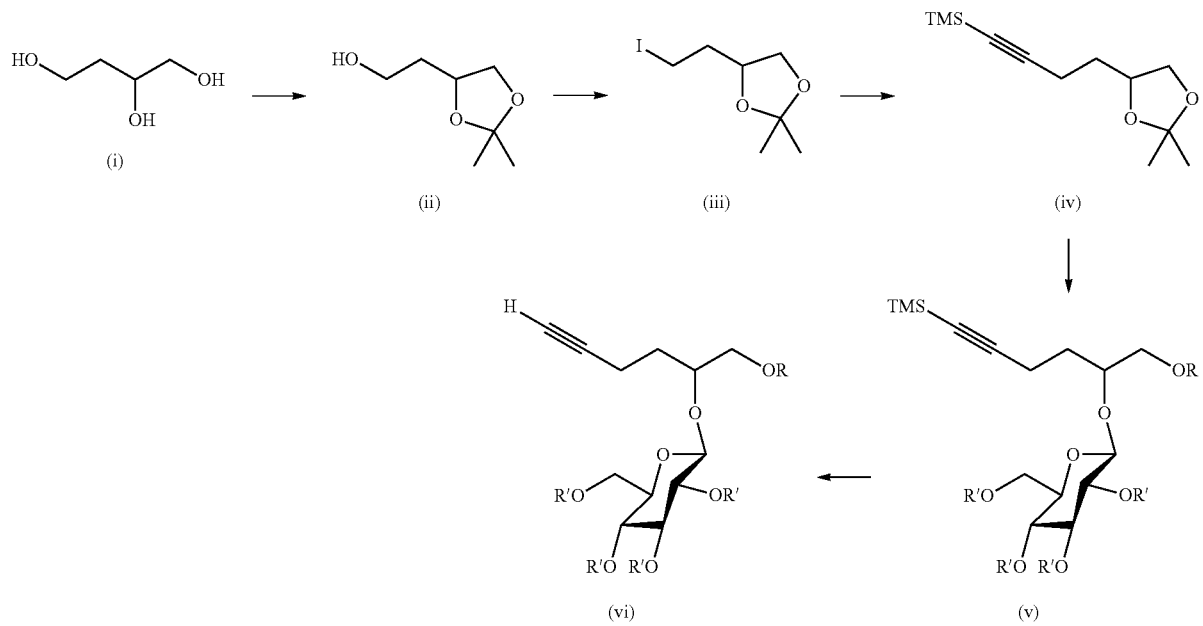

Butane-1,2,4-triol (i) is reacted with acetone to form a protected 1,2,4-triol compound (ii), which can be readily transformed to an iodo derivative (iii). Compound (iii) is then reacted with ethynyltrimethylsilane, under a basic condition (e.g., n-BuLi), to give (4-(2,2-dimethyl-1,3-dioxolan-4-yl)but-1-ynyl)trimethylsilane (iv). Compound (iv) is subsequently treated with an acid (e.g., acetic acid), followed by a coupling reaction with 2-bromoglucopyranose to afford an adduct (v). Compound (v) can be further treated with potassium fluoride to afford 2-phenyl-4H-chromen-4-one (vi).

Scheme 2

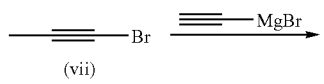

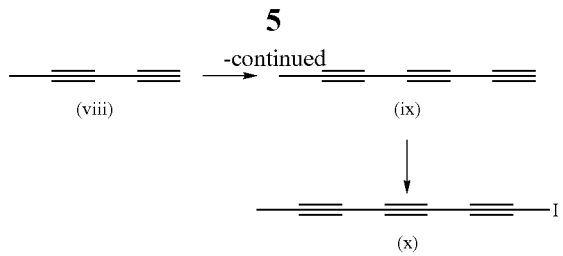

1-Bromoprop-1-yne (vii) is reacted with ethynylmagnesium bromide to afford penta-1,3-diyne (viii), which is further converted to hepta-1,3,5-triyne (ix). Compound (ix) can be readily transformed to 1-iodohepta-1,3,5-triyne (x) under a basic condition (e.g., n-BuLi), followed by addition of an iodo compound (e.g., $I_2$).

Scheme 3

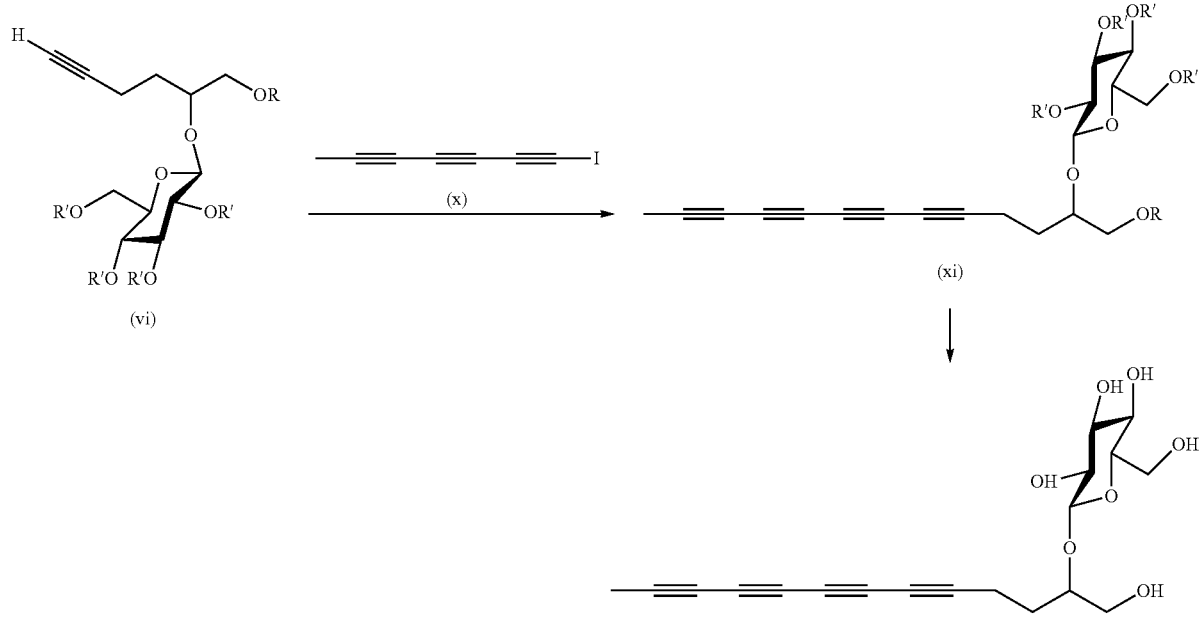

Scheme 3 demonstrates a coupling reaction between an acetylene derivative (vi), obtained from Scheme 1, and 1-iodohepta-1,3,5-triyne (x), obtained from Scheme 2, to a tetrayne compound (xi). Removal of protecting groups affords a polyacetylenic compound, 2β-D-glucopyranosyloxy-1-hydroxytrideca-5,7,9,11-tetrayne, a compound of this invention.

Synthetic chemistry transformations useful in synthesizing applicable compounds are described, for example, in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

This invention features a method of administrating an effective amount of one of the above-described polyacetylenic compounds or a *Bidens pilosa* preparation containing such a compound to a subject for treating type II diabetes. The term "treating" refers to administration of an effective amount of the compound of formula (I) to a subject, who has type II diabetes, or a symptom or predisposition toward such a disease, with the purpose to cure, alleviate, relieve, remedy, ameliorate, or prevent type II diabetes, the symptoms of it, or the predispositions towards it. Such a subject can be identified by a health care professional based on results from any suitable diagnostic method. "An effective amount" refers to the amount of an active thiophene compound that is required to confer a therapeutic effect on the treated subject. Effective doses will vary, as recognized by those skilled in the art, depending on route of administration, excipient usage, and the possibility of co-usage with other therapeutic treatment.

When treating type II diabetes with a polyacetylenic compound (either as a pure compound or in a *Bidens pilosa* extract), they can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

The polyacetylenic compounds described above lower blood glucose levels by enhancing insulin synthesis and insulin secretion. They can be preliminarily screened for their efficacy in treating type II diabetes by in vitro assays or by animal experiments, and then confirmed by clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Example 1

*Bidens pilosa* plants were collected from the campus of Academia Sinica, Taiwan. Approximately 10 kg of cleaned and crushed plants, in their entirety, was refluxed in 40 L of water for two hours. After removal of aqueous phase, insoluble materials was again refluxed in 25 L of water for two hours. The combined aqueous solutions (approximately 65 L) were evaporated in vacuo to yield a residue, which was subsequently suspended in 1.0 L of water and extracted with 1.0 L of n-butanol for three times. The n-butanol fraction was first evaporated on a vacuum rotary evaporator under reduced pressure and then lyophilized to provide a crude product of cytopiloyne (37.7 g).

The crude product was subsequently chromatographed over a RP-18 silica gel column with a $CH_3OH/H_2O$ gradient solvent system to give sub-fractions BPB1, BPB2, BPB3, and BPB4. The BPB3 fraction, eluted by 70% $CH_3OH$, was further fractioned by semi-preparative HPLC using a $CH_3OH/H_2O$ solvent system. Cytopiloyne was obtained and characterized by $^1H$ NMR and $^{13}C$ NMR.

$^1H$ NMR (500 MHz, $CDOD_3$) δ 1.78 (2H, q, J=6.8 Hz), 1.98 (3H, s), 2.58 (2H, t, J=6.8 Hz), 3.19 (1H, dd, J=9.1, 7.8 Hz), 3.30 (1H, m), 3.34 (1H, m), 3.59 (2H, m), 3.65 (1H, dd, J=12.0, 6.5 Hz), 3.75 (1H, p, J=6.8 Hz), 3.85 (1H, dd, J=12.0, 1.7 Hz), 4.32 (1H, d, J=7.8 Hz); $^{13}C$ NMR (125 MHz, $CDOD_3$) δ 3.8, 16.1, 31.4, 60.0, 60.9, 61.8, 62.4, 62.6, 64.9, 65.8, 66.2, 71.5, 75.2, 77.9, 81.6, 104.8.

Example 2

The db/db mice were purchased from Jackson Laboratory (Bar Harbor, Me., U.S.A.), and then maintained and handled according to the guidelines of Academia Sinica Institutional Animal Care and Utilization Committee (Taiwan).

Diabetic db/db mice of 7-8 weeks old were fasted for 12 hours (water allowed), and then intraperitoneally injected with phosphate-buffered saline (PBS) or cytopiloyne at 25 μg/kg, blood glucose levels in the mice were monitored at 0, 1, 2, 4, and 6 hours using Elite glucometer.

The results show that at two hours the blood glucose levels in treated mice significantly decreased.

Example 3

The db/db mice were purchased from Jackson Laboratory, and then maintained and handled according to the guidelines of Academia Sinica Institutional Animal Care and Utilization Committee (Taiwan). Glibenclamide was purchased from MP Biomedical Inc.

Diabetic db/db mice aged 7-8 weeks were fasted for 12 hours (water allowed) and orally administered with PBS, cytopiloyne at 0.5 mg/kg or Glimepiride at 2.5 mg/kg. Half an hour later, the mice were intraperitoneally injected with glucose at 0.5 g/kg body weight. Blood glucose levels were monitored at 0, 0.5, 1, 1.5, 2 and 3 hours using Elite glucometer.

The results show that cytopiloyne at 0.5 mg/kg body weight improved glucose tolerance as effectively as Glimepiride at 2.5 mg/kg body weight, as opposed to PBS in mice.

Example 4

RIN-m5F cells, a rat β cell line, were obtained from the American Type Culture Collection (ATCC). Glucose-free RPMI medium was purchased from Life Technology. The cells were grown in a glucose-free RPMI 1640 medium supplemented with 10% FCS, penicillin (100 U/ml), streptomycin (100 μg/ml), 2-mercapoethanol (50 μM), sodium pyruvate (1 mM), and glutamate (292 μg/ml).

The cells were separately incubated with vehicle, glucose at a high dose (16.7 mM), glucose at a low dose (3.6 mM), and cytopiloyne at 2.5, 10, and 15 μg/mL for 24 hours. Insulin levels in the cell medium were determined using an insulin Elisa kit (Mercodia, Uppsala, Sweden).

The results show that cytopiloyne significantly enhanced insulin secretion.

Example 5

RIN-m5F cells were pre-treated with vehicle, diazoxide (100 μM), EGTA (10 μM), or nimodipine (1 μM) for 30 minutes. They were then incubated with cytopiloyne at 5 μg/ml for 10 min. Insulin levels in the cell medium were determined using an insulin Elisa kit.

It was observed that diazoxide, a potassium/ATP channel opener, suppressed cytopiloyne-induced insulin secretion. EGTA, a calcium chelator, and nimodipine, a calcium channel blocker, suppressed cytopiloyne-mediated insulin secretion in β cells. These results suggest that cytopiloyne induced insulin secretion by affecting the functions of potassium/ATP channel and calcium channel.

Example 6

The pINS-DCR3 vector containing a human insulin promoter was digested by SphI and BamHI and then cloned into a pcDNAΔCMVlue vector to generate the plasmid pINS-Luc. The plasmid pRL-TK containing a thymidine kinase promoter and a *Renilla* luciferase reporter gene was purchased from Promega.

RIN-m5F cells transfected with pINS-Luc and pRL-TK plasmids were incubated with vehicle, high glucose (16.7 mM), or cytopiloyne at 2.5, 10, or 15 μg/ml for 24 hours.

The results show that cytopiloyne stimulated insulin transcription in RIN-m5F cells in a dose-dependent manner.

Example 7

Primary β cells from mice were seeded in 9-cm² plates in a glucose-free RPMI 1640 medium. Both mouse primary β cells and RIN-m5F cells were treated with vehicle or cytopiloyne at 2.5, 5, or 10 μg/ml for 24 hours. The treated cells were subsequently subjected to intracellular staining with anti-insulin antibody (H86, Santa Cruz Biotechnology, CA, USA) and FITC-conjugated anti-rabbit antiserum (BD Biosciences, CA, USA) according to the manufacturer's instruction. The insulin levels in the cell media were determined using an insulin Elisa kit.

The results show that cytopiloyne elevated insulin levels in μ cells in comparison with vehicle treatment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating type II diabetes, comprising administering to a subject in need thereof an effective amount of *Bidens pilosa* extract, comprising an isolated compound cytopiloyne having a chemical structure of and further wherein the extract comprises 2.5 μg/ml or more of the isolated cytopiloyne.

* * * * *

UNITED STATES PATENT AND TRADEMARK OFFICE
CERTIFICATE OF CORRECTION

PATENT NO. : 8,147,880 B2
APPLICATION NO. : 12/766895
DATED : April 3, 2012
INVENTOR(S) : Wen-Chin Yang Page 1 of 1

It is certified that error appears in the above-identified patent and that said Letters Patent is hereby corrected as shown below:

On the Title Page, Item (54), and Column 1, line 2, title delete "EXRESSION" and substitute --EXPRESSION--.

Signed and Sealed this
Twenty-eighth Day of August, 2012

David J. Kappos
*Director of the United States Patent and Trademark Office*